(12) United States Patent
Tinger et al.

(10) Patent No.: US 9,249,068 B2
(45) Date of Patent: Feb. 2, 2016

(54) PROCESS FOR THE PRODUCTION OF XYLENES

(71) Applicant: ExxonMobil Chemical Patents Inc., Baytown, TX (US)

(72) Inventors: Robert G. Tinger, Friendswood, TX (US); Jeffrey L. Andrews, Houston, TX (US); Michel Molinier, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/735,531

(22) Filed: Jun. 10, 2015

(65) Prior Publication Data

US 2015/0376086 A1    Dec. 31, 2015

Related U.S. Application Data

(60) Provisional application No. 62/018,724, filed on Jun. 30, 2014, provisional application No. 62/018,726, filed on Jun. 30, 2014.

(51) Int. Cl.
*C07C 2/66* (2006.01)
*C07C 6/12* (2006.01)
(Continued)

(52) U.S. Cl.
CPC .............. *C07C 2/864* (2013.01); *B01J 19/245* (2013.01); *C07C 2/862* (2013.01); *C07C 4/12* (2013.01);
(Continued)

(58) Field of Classification Search
CPC .............. C07C 2/66; C07C 6/12; C07C 1/24; C07C 4/24; C07C 5/27

USPC ................... 585/323, 467, 469, 470, 478, 483
See application file for complete search history.

(56) References Cited

U.S. PATENT DOCUMENTS

| 4,886,930 A | 12/1989 | Zinnen |
|---|---|---|
| 4,956,522 A | 9/1990 | Zinnen |

(Continued)

FOREIGN PATENT DOCUMENTS

| WO | WO 2013/085681 | 6/2013 |
|---|---|---|
| WO | WO 2014/058550 | 4/2014 |

OTHER PUBLICATIONS

U.S. Appl. No. 62/018,724, filed Jun. 30, 2014, Molinier et al.

(Continued)

*Primary Examiner* — Thuan D Dang
(74) *Attorney, Agent, or Firm* — Amanda K. Jenkins

(57) ABSTRACT

In a process for producing para-xylene, a feed stream comprising $C_{6+}$ aromatic hydrocarbons is separated into a $C_{7-}$ aromatic hydrocarbon-containing stream, a $C_8$ aromatic hydrocarbon-containing stream, and a $C_{9+}$ aromatic hydrocarbon-containing stream. The $C_{7-}$ aromatic hydrocarbon-containing stream is contacted with a methylating agent to convert toluene to xylenes and produce a methylated effluent stream. Ethylbenzene is removed from the $C_8$ aromatic hydrocarbon-containing stream, para-xylene is recovered from the ethylbenzene-depleted $C_8$ aromatic hydrocarbon-containing stream and the methylated effluent stream in a para-xylene recovery section to produce a para-xylene depleted stream, which is then contacted with a xylene isomerization catalyst under liquid phase conditions effective to isomerize xylenes in the para-xylene depleted stream and produce an isomerized stream. The $C_{9+}$-containing stream with a transalkylation catalyst under conditions effective to convert $C_{9+}$-aromatics to $C_{8-}$-aromatics and produce a transalkylated stream, which is recycled together with the isomerized stream to the para-xylene recovery section.

12 Claims, 2 Drawing Sheets

(51) Int. Cl.
*C07C 1/24* (2006.01)
*C07C 4/24* (2006.01)
*C07C 5/27* (2006.01)
*C07C 2/86* (2006.01)
*C07C 4/12* (2006.01)
*C07C 6/06* (2006.01)
*B01J 19/24* (2006.01)

(52) U.S. Cl.
CPC .............. *C07C 5/2729* (2013.01); *C07C 6/06* (2013.01); *B01J 2219/24* (2013.01); *C07C 2529/40* (2013.01)

(56) References Cited

U.S. PATENT DOCUMENTS

| | | |
|---|---|---|
| 5,057,643 A | 10/1991 | Zinnen |
| 5,516,956 A | 5/1996 | Abichandani et al. |
| 5,563,310 A | 10/1996 | Chang et al. |
| 5,625,103 A | 4/1997 | Abichandani et al. |
| 6,423,879 B1 | 7/2002 | Brown et al. |
| 6,504,072 B1 | 1/2003 | Brown et al. |
| 6,642,426 B1 | 11/2003 | Johnson et al. |
| 7,663,010 B2 | 2/2010 | Levin |
| 7,989,672 B2 | 8/2011 | Kinn et al. |
| 9,012,711 B2 | 4/2015 | Ou et al. |
| 2010/0228066 A1* | 9/2010 | Kong ............. C10G 67/06 585/321 |
| 2011/0009682 A1 | 1/2011 | Matsushita et al. |
| 2011/0263918 A1 | 10/2011 | Ou et al. |
| 2011/0319688 A1 | 12/2011 | Ou |
| 2012/0316375 A1 | 12/2012 | Zheng et al. |
| 2013/0296624 A1 | 11/2013 | Iaccino et al. |
| 2014/0100402 A1 | 4/2014 | Gawlik et al. |

OTHER PUBLICATIONS

U.S. Appl. No. 62/018,726, filed Jun. 30, 2014, Molinier et al.

* cited by examiner

PROCESS FOR THE PRODUCTION OF XYLENES

CROSS REFERENCE TO RELATED APPLICATIONS

The present application claims priority to and the benefit of U.S. Provisional Application Nos. 62/018,724 and 62/018,726, both filed Jun. 30, 2014, which are incorporated by reference in their entirety.

FIELD OF THE INVENTION

This invention relates to a process for the production of xylenes and particularly for the production of para-xylene.

BACKGROUND OF THE INVENTION

A major source of xylenes is catalytic reformate, which is produced by contacting petroleum naphtha with a hydrogenation/dehydrogenation catalyst on a support. The resulting reformate is a complex mixture of paraffins and $C_6$ to $C_8$ aromatics, in addition to a significant quantity of heavier aromatic hydrocarbons. After removing the light ($C_5-$) paraffinic components, the remainder of reformate is normally separated into $C_{7-}$, $C_8$, and $C_{9+}$-containing fractions using a plurality of distillation steps. Benzene can then be recovered from the $C_{7-}$-containing fraction to leave a toluene-rich fraction which is generally used to produce additional $C_8$ aromatics by toluene disproportionation and/or transalkylation with part of the $C_{9+}$-aromatics containing fraction. The $C_8$-containing fraction is fed to a xylene production loop where para-xylene is recovered, generally by adsorption or crystallization, and the resultant para-xylene depleted stream is subjected to catalytic conversion to isomerize the xylenes back towards equilibrium distribution. The resultant isomerized xylene stream can then be recycled to the para-xylene recovery unit.

Although benzene and toluene are important aromatic hydrocarbons, the demand for xylenes, particularly para-xylene, outstrips that for benzene and toluene and currently is growing at an annual rate of 5-7%. There is, therefore, a continuing need to develop aromatics production technologies which maximize the production of para-xylene, while minimizing the associated capital and operating costs.

SUMMARY OF THE INVENTION

According to the present invention, an improved method of producing para-xylene, optionally together with benzene and/or ortho-xylene, has now been developed in which a methylation unit is added to a para-xylene production complex to convert toluene and/or benzene in a reformate or similar aromatics fraction to additional xylenes. The methylation unit produces a $C_8$ aromatic product rich in para-xylene, but with little or no additional ethylbenzene. As a result, the production and operating costs of the xylenes separation section can be reduced and less costly liquid phase processes can be used for the xylene isomerization section. The amount of ethylbenzene in the process can be managed by the addition of a high conversion ethylbenzene removal unit upstream of the $C_8$ fractionation section and/or by feeding part of the para-xylene depleted stream to the transalkylation unit. The high conversion ethylbenzene removal unit may operate on low pressure, once-through hydrogen, omitting the need for facilities for the recovery and recycle of hydrogen. Removing ethylbenzene prior to the xylenes isomerization section allows for only liquid phase isomerization to be used, minimizing operating costs, and because liquid phase isomerization produces less $C_{9+}$ aromatics than vapor phase isomerization, the isomerized stream may bypass the xylenes fractionation column resulting in even lower operating costs.

Thus, in one aspect, the invention resides in a process for producing para-xylene, in which a feed stream comprising $C_{6+}$ aromatic hydrocarbons is separated into at least a toluene-containing stream, a $C_8$ aromatic hydrocarbon-containing stream, and a $C_{9+}$ aromatic hydrocarbon-containing stream. At least part of the toluene-containing stream is contacted with a methylating agent under conditions effective to convert toluene to xylenes and produce a methylated effluent stream, and at least part of the $C_8$ aromatic hydrocarbon-containing stream is subjected to ethylbenzene removal. Para-xylene is recovered from the $C_8$ aromatic hydrocarbon-containing stream and the methylated effluent stream to produce at least one para-xylene depleted stream. At least part of the para-xylene depleted stream is contacted with a xylene isomerization catalyst under liquid phase conditions effective to isomerize xylenes in the para-xylene depleted stream and produce an isomerized stream, which is recycled to the para-xylene recovery step. At least part of the $C_{9+}$-containing stream is contacted with a transalkylation catalyst under conditions effective to convert $C_{9+}$-aromatics to $C_{8-}$-aromatics and produce a transalkylated stream, which is recycled to one or more of the toluene methylation step and para-xylene recovery step.

In a further aspect, the invention resides in an apparatus for producing para-xylene comprising a catalytic reformer for producing a reformate stream comprising $C_{6+}$ aromatic hydrocarbons; a first separation system for separating the reformate stream into at least a toluene-containing stream, a $C_8$ aromatic hydrocarbon-containing stream and a $C_{9+}$ aromatic hydrocarbon-containing stream; a toluene methylation unit for converting toluene in the toluene-containing stream to xylenes and produce a methylated effluent stream; an ethylbenzene removal unit for dealkylating the ethylbenzene to benzene; a second separation system for recovering para-xylene from the $C_8$ aromatic hydrocarbon-containing stream and the methylated effluent stream and a transalkylation effluent stream to produce at least one para-xylene depleted stream; a liquid phase xylene isomerization unit for isomerizing xylenes in the at least one para-xylene depleted stream to produce a first isomerized stream; a recycle system for recycling at least part of the first isomerized stream to the second separation system; and a transalkylation unit for converting $C_{9+}$ aromatics in the $C_{9+}$ aromatic hydrocarbon-containing stream to $C_{8-}$ aromatics and produce the transalkylation effluent stream.

DETAILED DESCRIPTION OF THE EMBODIMENTS

Figure 1:
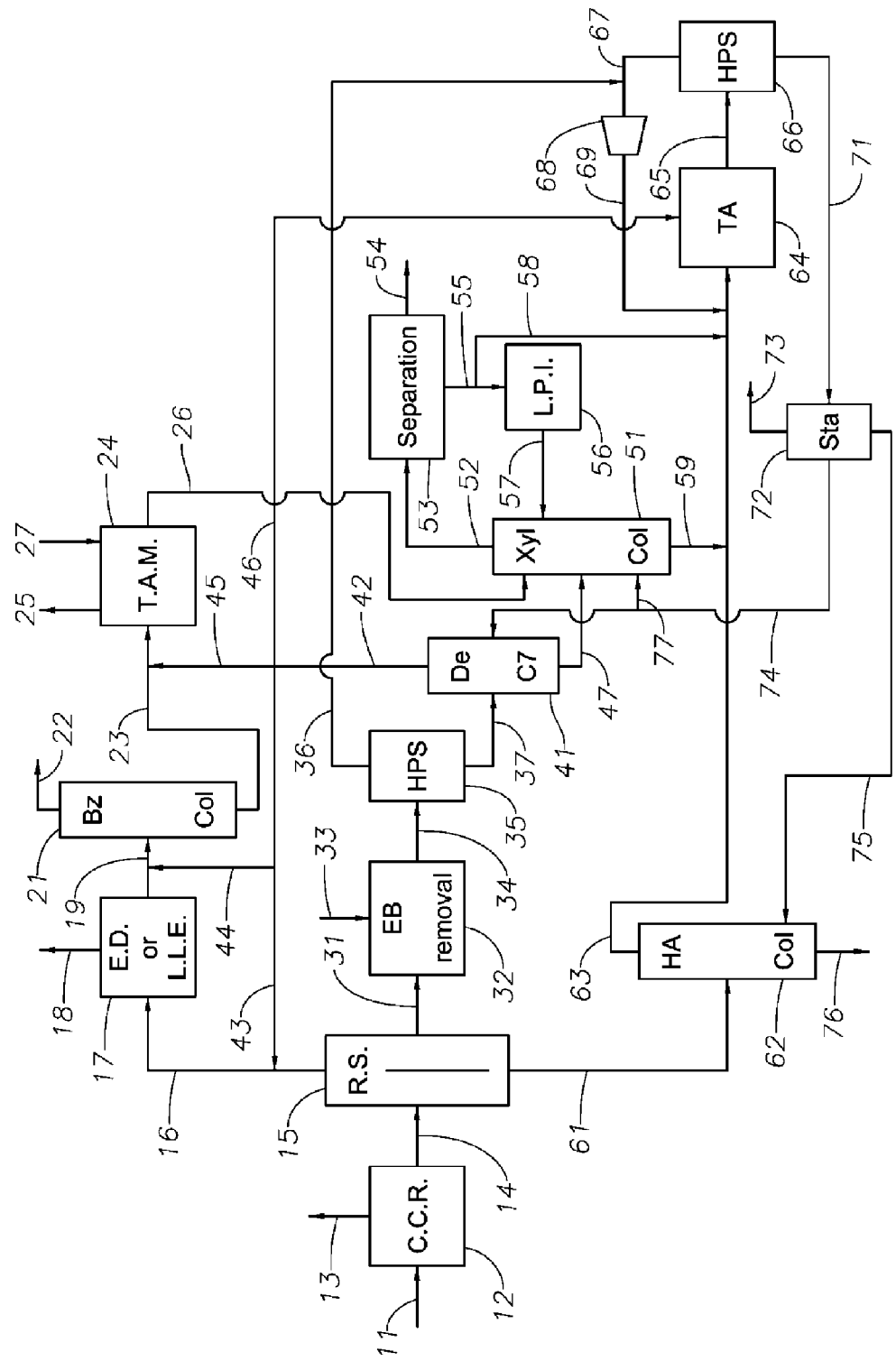
FIG. 1 is a flow diagram of a process for producing para-xylene from catalytic reformate according to a first embodiment of the invention.

The present invention describes a method and apparatus for producing para-xylene, optionally together with benzene and/or ortho-xylene, from a reformate or similar aromatics fraction. In the present process, a methylation unit is added to a para-xylene production complex to convert toluene and/or benzene in the reformate fraction to additional xylenes. Since the methylation unit can produce a $C_8$ aromatic product rich in para-xylene with little or no additional ethylbenzene, the production and operating costs of the xylenes separation section can be reduced and less costly liquid phase processes can be used in the xylene isomerization section. The amount of ethylbenzene in the process can be managed by the addition of a high conversion ethylbenzene removal unit upstream of the $C_8$ fractionation section and/or by feeding part of the para-xylene depleted stream to the transalkylation unit.

Any method known in the art for adding methyl groups to a phenyl ring in a fixed-bed, fluidized bed, or moving bed process can be used in the methylation step of the present process. However, in certain preferred embodiments, the methylation step follows a process such as that described in U.S. Pat. No. 5,563,310 or 6,642,426, and employs a highly para-selective methylation catalyst, such as that employed in U.S. Pat. Nos. 6,423,879 and 6,504,072, the entire contents of which are incorporated herein by reference. Such a catalyst comprises a molecular sieve having a Diffusion Parameter for 2,2-dimethylbutane of about 0.1-15 $sec^{-1}$, such as 0.5-10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient ($cm^2/sec$) and r is the crystal radius (cm). The required diffusion parameters can be derived from sorption measurements provided the assumption is made that the plane sheet model describes the diffusion process. Thus, for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967, the entire contents of which are incorporated herein by reference.

The molecular sieve employed in the para-selective methylation process is normally a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are particularly effective for the present methylation process since the size and shape of their pores favor the production of p-xylene over the other xylene isomers. Conventional forms of these zeolites have Diffusion Parameter values in excess of the 0.1-15 $sec^{-1}$ range referred to above. However, the required diffusivity for the catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, such as at least one oxide selected from elements of Groups 2 to 4 and 13 to 16 of the Periodic Table. Most preferably, said at least one oxide modifier is selected from oxides of boron, magnesium, calcium, lanthanum, and most preferably phosphorus. In some cases, the zeolite may be combined with more than one oxide modifier, for example, a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier into the catalyst is conveniently achieved by the methods described in U.S. Pat. Nos. 4,356,338, 5,110,776, 5,231,064, and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Suitable phosphorus compounds include, but are not limited to, phosphonic, phosphinous, phosphorous and phosphoric acids, salts and esters of such acids, and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours. Similar techniques known in the art can be used to incorporate other modifying oxides into the catalyst employed in the alkylation process.

In addition to the zeolite and modifying oxide, the catalyst employed in the methylation process may include one or more binder or matrix materials resistant to the temperatures and other conditions employed in the process. Such materials include active and inactive materials such as clays, silica, and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite. Preferably, the matrix material comprises silica or a kaolin clay.

The methylation catalyst used in the present process may optionally be precoked. The precoking step may be carried out by initially loading uncoked catalyst into the methylation reactor. Then, as the reaction proceeds, coke is deposited on the catalyst surface and thereafter may be controlled within a desired range, typically from about 1 to about 20 wt % and preferably from about 1 to about 5 wt %, by periodic regeneration through exposure to an oxygen-containing atmosphere at an elevated temperature.

Methylation of toluene in accordance with the present process can be effected with any known methylating agent, but preferred methylating agents include methanol and/or a mixture of carbon monoxide and hydrogen.

Suitable conditions for the methylation reaction include a temperature from 350 to 700° C., such as from 500 to 600° C., a pressure of from 100 and 7000 kPa absolute, a weight hourly space velocity of from 0.5 to 1000 $hr^{-1}$, and a molar ratio of toluene to methanol (in the reactor charge) of at least about 0.2, e.g., from about 0.2 to about 20. The process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in a catalyst regenerator. One example of a suitable fluidized bed process for methylating toluene includes staged injection of the methylating agent at one or more locations downstream of the toluene feed location. Such a process in described in U.S. Pat. No. 6,642,426, the entire contents of which are incorporated herein by reference.

Using the present process, toluene can be alkylated with methanol so as to produce para-xylene at a selectivity of at least about 75 wt % (based on total $C_8$ aromatic product) at a per-pass aromatic conversion of at least about 15 wt % and a trimethylbenzene production level less than 1 wt %. Unreacted toluene and methylating agent and a portion of the water by-product may be recycled to the methylation reactor and heavy byproducts routed to fuels dispositions. The $C_8$ fraction is routed to a para-xylene separation section, which typically operates by fractional crystallization or by selective adsorption or both to recover a para-xylene product stream from the alkylation effluent and leave a para-xylene-depleted stream containing mainly $C_7$ and $C_8$ hydrocarbons. Since the toluene methylation unit enhances the para-xylene content of the reformate $C_8$ fraction, the size of the para-xylene separation section can be reduced. This is a significant advantage since the para-xylene separation section is one of the most expensive processes in an aromatics complex both from a capital cost and from an operating expense perspective.

After recovery of para-xylene in the para-xylene separation section, the remaining para-xylene-depleted stream is isomerized back to equilibrium before being recycled back to the para-xylene separation section. In the present process, isomerization of the para-xylene-depleted stream is conducted solely in a liquid phase isomerization unit, which minimizes operating costs. Any liquid phase catalytic isomerization process known to those skilled in the art can be used in the liquid phase xylene isomerization unit, but one preferred catalytic system is described in U.S. Pat. Nos. 8,697,929 and 8,569,559, the entire contents of each of which are incorporated herein by reference. Suitable conditions for the liquid phase isomerization process used herein include a temperature from about 230° C. to about 300° C. and a pressure from about 1300 to about 3500 kPa selected to maintain the para-xylene-depleted stream substantially in the liquid phase. In some embodiments, the weight hourly space velocity (WHSV) may be from about 0.5 to about 10 $hr^{-1}$.

The present process also employs a transalkylation unit to convert $C_9$ aromatics, $C_{10}$ aromatics and some $C_{11}$ aromatics in the reformate feed to equilibrium xylenes either directly or by reaction with benzene or toluene routed from other parts of the process. The xylenes in the transalkylation effluent can then be fed to the para-xylene separation section for recovery of para-xylene, while any benzene or toluene produced in the transalkylation process is conveniently supplied to the toluene methylation unit for further upgrading to additional xylenes. Any liquid phase or vapor phase transalkylation unit can be used in the present process, but one preferred unit employs the multi-stage catalytic system described in U.S. Pat. No. 7,663,010, the entire contents of which are incorporated herein by reference. The transalkylation unit can be used to generate benzene and toluene using xylenes and $C_{9+}$ aromatic feeds as described in U.S. Patent Application Publication No. 2012/0149958, the entire contents of which are incorporated herein by reference, of which the benzene and/or toluene can be used as feed to the toluene methylation unit to produce higher para-xylene purity feeds to the para-xylene recovery stages. Additionally, some of or all off site benzene, or import benzene feeds, can be transalkylated with $C_{9+}$ aromatic feeds to generate toluene and/or xylenes. Finally, the $C_{9+}$ aromatic molecules can be fractionated into a concentrated $C_9$ stream consisting of propylbenzenes and methylethylbenzenes which is transalkylated with benzene to produce toluene and ethylbenzenes. The toluene and ethylbenzene can then be processed in the toluene methylation unit to generate paraxylene and light olefins for recovery. The invention will now be more particularly described with reference to the accompanying drawings.

FIG. 1 illustrates a process for producing para-xylene according to a first embodiment of the invention, in which a naphtha feedstock is supplied by line 11 to a catalytic reformer 12 (for example, a semi-regenerative reformer, a cycle reformer or a continuous catalytic reformer). The effluent from the catalytic reformer 12 is a complex mixture of aliphatic and aromatic hydrocarbons and, after removal of the $C_{5-}$ fraction in a depentanizer (not shown), the remaining $C_{6+}$ fraction is fed by line 14 to a reformate splitter 15. Hydrogen is also generated in the catalytic reformer 12 and is removed via line 13 for use in the gas phase isomerization section described below, or in various units in a refinery, or in a cyclohexane unit or any other petrochemical process if the aromatics complex is not located next to a refinery. Alternatively, the hydrogen can be sold as export, or used in fuel, or flared.

The reformate splitter 15, which can optionally be a dividing-wall distillation column, separates the $C_{6+}$ fraction in line 14 into a $C_{7-}$-containing overhead stream, a $C_8$ containing intermediate stream, and a $C_{9+}$-containing bottoms stream. The $C_{6-}$-containing overhead stream may also contain some or all of the toluene and/or $C_8$ aromatics present in line 14 along with their non-aromatic co-boilers, depending on specific economic objectives.

The $C_{7-}$-containing overhead stream from the reformate splitter 15 is sent via line 16 to an extraction section 17, which can be a liquid-liquid extraction process, an extractive distillation type process or a hybrid thereof. Non-aromatics raffinate is removed from the extraction section 17 via line 18 and can be used in an olefins oligomerization or reformate alkylation unit, or as feed to a steam cracker or to the refinery gasoline pool, or as fuel. The raffinate can also be used as feed to an aromatization unit to produce additional aromatic molecules while generating hydrogen. The aromatics product from extraction section 17 is removed via line 19 and is supplied to a benzene column 21, optionally after pretreatment with clay or a molecular sieve catalyst to remove trace olefins or other low level impurities. Entrained water is removed from the aromatics extraction product in benzene column 21 and a benzene product is collected via line 22, typically as a sidestream from the top portion of the benzene column 21.

The benzene column bottoms product is rich in toluene, although it may also contain some trace xylenes and heavier alkylaromatics, and is sent via line 23 to a toluene methylation section 24. The benzene in line 22 can either be recovered for sale or hydrogenation to produce cyclohexane or can be fed to the toluene methylation section 24 for additional xylenes production. In the toluene methylation section 24, toluene from line 23, optionally together with benzene from column 21, is reacted with methanol injected via line 25 to produce xylenes and water. The process off-gas from the toluene methylation section 24 is collected by line 27 and can be used in an olefins oligomerization unit or a reformate alkylation unit, or can be sent to a steam cracker or refinery for olefins recovery, or used as fuel gas. Preferred processes for treating and recovering the off-gas stream are disclosed in U.S. Patent Publication No. 2014/0100402 and U.S. Provisional Patent Application No. 62/041,717.

The remainder of the product from the toluene methylation section 24 is fed via line 26 to a xylene distillation column 51, which divides the methylation product into a para-xylene rich $C_8$ aromatics overhead stream and a $C_{9+}$ bottoms stream. The para-xylene rich $C_8$ aromatics overhead stream from the xylene distillation column 51 is sent via line 52 to a separation section 53, where para-xylene product is recovered via line 54. The product of the toluene methylation section 24 may require treatment to remove oxygenate by-products, preferably prior to the separation section 53. Thus, the product in line 26 or overheads from the xylene distillation column 51 in line 52 may be subjected to oxygenate removal technology, such as that described in U.S. Pat. No. 9,012,711 or U.S. Patent Publication No. 2013/0324779, the entire contents of which are incorporated herein by reference.

The separation section 53 can be based on an adsorption process or a crystallization process or any combination of both, but in any case it can be optimized to manage para-xylene separation from three separate streams, namely one with ~20% para-xylene content ($C_8$ portion of the reformate), one with preferably ≥75% para-xylene content (toluene methylation process effluent), and one with equilibrium (~24%) para-xylene content (transalkylation and/or isomerization effluent). Such optimization will result in substantial downsizing of the overall separation section 53 as well as considerable savings in utilities consumption. Such optimization may include feeding the para-enriched xylenes stream independent of equilibrium xylenes stream as described in U.S. Pat. Nos. 8,168,845; 8,529,757; 8,481,798; 8,569,564; 8,580,120; U.S. Patent Application Publication No. 2012/0241384; and U.S. patent application Ser. No. 14/580,452, the entire contents of which are incorporated herein by reference. Alternatively, a para-xylene enriched product or intermediate product from the adsorption process, which has a para-xylene purity less than 99.7 wt %, can be fed to the crystallization unit to enrich the para-xylene to higher concentrations. Likewise, the crystallization product or intermediate product having a para-xylene purity less than 99.7 wt % may be fed to the adsorption process to enrich the para-xylene to higher concentrations.

Invariably there will be a small amount of toluene present in the xylenes feed to the para-xylene separation section 53. If a simulated moving bed (SMB) adsorption unit is used to recover para-xylene, a fraction of the toluene present in the xylenes feed will be fractionated as a "crude" toluene product, which may contain trace amounts of xylenes or water. This stream can be sent directly to the toluene methylation section 24 without any treatment to remove trace xylenes or water, since the feed to the toluene methylation section 24 generally contains water co-feed to improve methanol utilization and to suppress feed preheat coking. A combination of both an adsorption process and a crystallization process in separation section 53 may include a small SMB unit (not shown) and a small crystallization unit (not shown) operating in series or in parallel, with the SMB unit primarily dedicated to para-xylene separation from equilibrium xylenes streams and the crystallization unit primarily dedicated to para-xylene separation from the para-xylene enriched stream.

After recovery of the para-xylene, the remaining liquid phase para-xylene depleted effluent from the separation section 53 is collected via line 55 and can be fed in the liquid phase to a liquid phase xylenes isomerization section 56 where xylenes are isomerized to equilibrium. The effluent from the liquid phase isomerization section 56 contains close to equilibrium para-xylene (~24%) and is supplied by line 57 to a xylene rerun column 51. A $C_8$-rich overhead stream is removed as overhead from the xylene rerun column 51 and is fed via line 52 to separation section 53 where para-xylene product is collected via line 54. In case of accumulation of ethylbenzene in the xylenes loop constituted by xylene column 51, line 52, separation section 53, line 55, liquid phase isomerization section 56, and line 57, an ethylbenzene purge line 58 has been added and can be used to redirect a portion of the separation section 53 effluent to transalkylation section 64 where ethylbenzene will be dealkylated to benzene. In alternate embodiments (not shown), the ethylbenzene purge line 58 may be redirected to ethylbenzene removal unit 32 or toluene methylation section 24.

In some embodiments (not shown), the effluent from the liquid phase isomerization section 56 can be sent directly to separation section 53 (without separation in the xylene rerun column 51) provided the concentration of heavy aromatics produced across the liquid phase isomerization section 56 is within the specification of the separation process used in separation section 53. U.S. Pat. No. 7,989,672, the entire contents of which are incorporated herein by reference, teaches the maximum allowable $C_{9+}$ aromatics concentration for a crystallization unit, which can also apply within limits to a simulated moving bed adsorption process, or hybrids of a crystallization and a simulated moving bed adsorption process.

The $C_8$ stream from reformate splitter 15, which also contains some $C_9$ impurities, is collected in line 31 and sent to ethylbenzene removal unit 32, where ethylbenzene is dealkylated to benzene. Although ethylbenzene removal can be carried out in liquid phase, it is preferably achieved in gas phase. Hydrogen is fed to the ethylbenzene removal unit 32 via line 33. Preferably, once-through low pressure hydrogen is used, thereby eliminating facilities for the recovery and recycle of hydrogen. In the ethylbenzene removal unit, the preferred catalyst is the first catalyst used in the dual bed catalyst system described in U.S. Pat. No. 5,516,956 or 7,663,010. However, other catalytic processes that accomplish dealkylating ethylbenzene to benzene known to those skilled in the art could be utilized. The ethylbenzene removal process is preferably operated at conditions maximizing ethylbenzene conversion per pass, preferably >80 wt % conversion per pass, and even more preferably >90 wt % conversion per pass, in order to minimize ethylbenzene circulation in the xylene loop. Operating conditions for the ethylbenzene removal section 32 will also be chosen as to minimize undesirable transalkylation reactions leading to xylene losses to $C_7$, $C_9$, or $C_{10}$ aromatics. However, low xylene losses are not critical for the ethylbenzene removal unit operation, since toluene collected in deheptanizer column 41 overhead will be converted to xylenes in toluene methylation section 24, and $C_9$ or $C_{10}$ aromatics collected in xylene column 51 bottoms will be converted to xylenes in transalkylation section 64.

The effluent from ethylbenzene removal section 32 is fed to high pressure separator 35 via line 34. Hydrogen-rich light gas from the high pressure separator 35 is collected via line 36 and can be fed to the suction line 67 of the recycle gas compressor 68 in the transalkylation process recycle gas, as depicted in FIG. 1, optionally through a booster compressor if necessary. The bottoms stream from the high pressure separator 35 is fed via line 37 to deheptanizer column 41 or optionally to the stabilizer column 72 (line not shown). The overhead of the deheptanizer column, collected in line 42, mostly contains $C_6$ and $C_7$ aromatics and could be sent to one or more of four locations depending on the composition of the overhead stream and overall complex economics. If benzene co-boilers content is high and high purity benzene production must be maximized, the overhead stream can be directed to extraction section 17 via line 43. Or, if benzene production must be maximized but benzene co-boilers content is such that overall complex benzene purity will be acceptable without extraction, then the stream can be directly routed to benzene column 21 via line 44. Alternatively, if there is no need to maximize benzene production, then the stream can be directed to toluene methylation unit 24 via line 45 or to transalkylation unit 64 via line 46 for additional production of xylenes. The bottoms stream of the deheptanizer column is fed via line 47 to xylene column 51. In xylene column 51, $C_8$ aromatics are collected overhead and fed to the xylene loop via line 52, while $C_{9+}$ aromatics are collected from the bottom of the column and routed to transalkylation unit 64 via line 59.

The $C_{9+}$ bottoms stream from the reformate splitter 15 is sent via line 61 to the heavy aromatics column 62, which separates $C_9$ aromatics, $C_{10}$ aromatics and some $C_{11}$ aromatics overhead and feeds these components via line 63 to a transalkylation section 64, while heavier compounds are collected via line 76 for supply to the fuel oil pool and/or to another hydrocarbon processing unit which may be able to upgrade the heavier compounds to a more desirable, valuable product, or products.

The overhead of the heavy aromatics column 62 may be combined with the $C_{9+}$ aromatics collected from the bottom of the xylenes column 51 in line 59, the ethylbenzene purge stream from the liquid phase isomerization unit 56 in line 58, and optionally at least a portion of the overhead 42 from the deheptanizer column 41 in line 46 prior to the transalkylation unit 64. In the transalkylation section 64, $C_9$ aromatics, $C_{10}$ aromatics, and some $C_{11}$ aromatics are converted to equilibrium xylenes either directly or by reaction with benzene or toluene routed from other parts of the process. While there are many options to optimize para-xylene production in an aromatics complex operating a toluene methylation unit (such as toluene methylation section 24) and a transalkylation unit (such as transalkylation section 64), since toluene methylation is highly selective to paraxylene, and transalkylation produces a mixed xylenes product, in a preferred embodiment, all toluene introduced or produced in the aromatics complex is sent to the toluene methylation section 24 rather than the transalkylation section 64. Toluene sources in the complex, illustrated in FIG. 1, include toluene from the benzene column 21 in line 23, unconverted toluene in the effluent from the toluene methylation section, "crude" toluene from the para-xylene separation section 53, and toluene produced in the transalkylation section 64. Thus, little or no toluene in the effluent from the transalkylation section 64 is recycled to the transalkylation section 64. In the preferred embodiment, benzene from benzene column 21 is sent to transalkylation section 64 (not shown in FIG. 1) in an amount that optimizes the methyl to ring ratio such that xylenes production in said unit is maximized. The benzene that is not processed in transalkylation section 64 can be recovered for sale or hydrogenation to produce cyclohexane or can be fed to the toluene methylation section 24 for additional xylenes production.

The effluent from the transalkylation section 64 is supplied by line 65 to high pressure separator 66 where hydrogen-rich gas is collected and recycled to the transalkylation unit 64 via line 67, recycle compressor 68, and line 69. The bottoms stream from the high pressure separator 66 is fed via line 71 to stabilizer column 72, which can optionally be a dividing-wall column. Light gas from the stabilizer column is collected via line 73. The bottoms stream from the stabilizer column 72, containing mostly $C_{9+}$ aromatics, is fed via line 75 to heavy aromatics column 62 where lighter components will be recycled to transalkylation unit 64 and heavier compounds will be sent to the fuel oil pool as described above. A $C_6$-$C_8$ product stream is collected as a side-stream and sent to the deheptanizer column 41 via line 74. When benzene and toluene content is low, stream 74 can partially or completely be redirected to xylene column 51 via line 77.

Optionally, where ortho-xylene production is desired, part or all of the bottoms stream from the xylene rerun column 51 can be fed to an orthoxylene column (not shown). Orthoxylene product may be collected overhead, while the orthoxylene column bottoms heavies may be sent to the transalkylation section 64 or optionally heavy aromatics column 62. If excessive ortho-xylene is produced above production needs, a portion or all of the orthoxylene can be processed across the liquid phase isomerization section 56 or transalkylation section 64 to produce more para-xylene.

Figure 2:
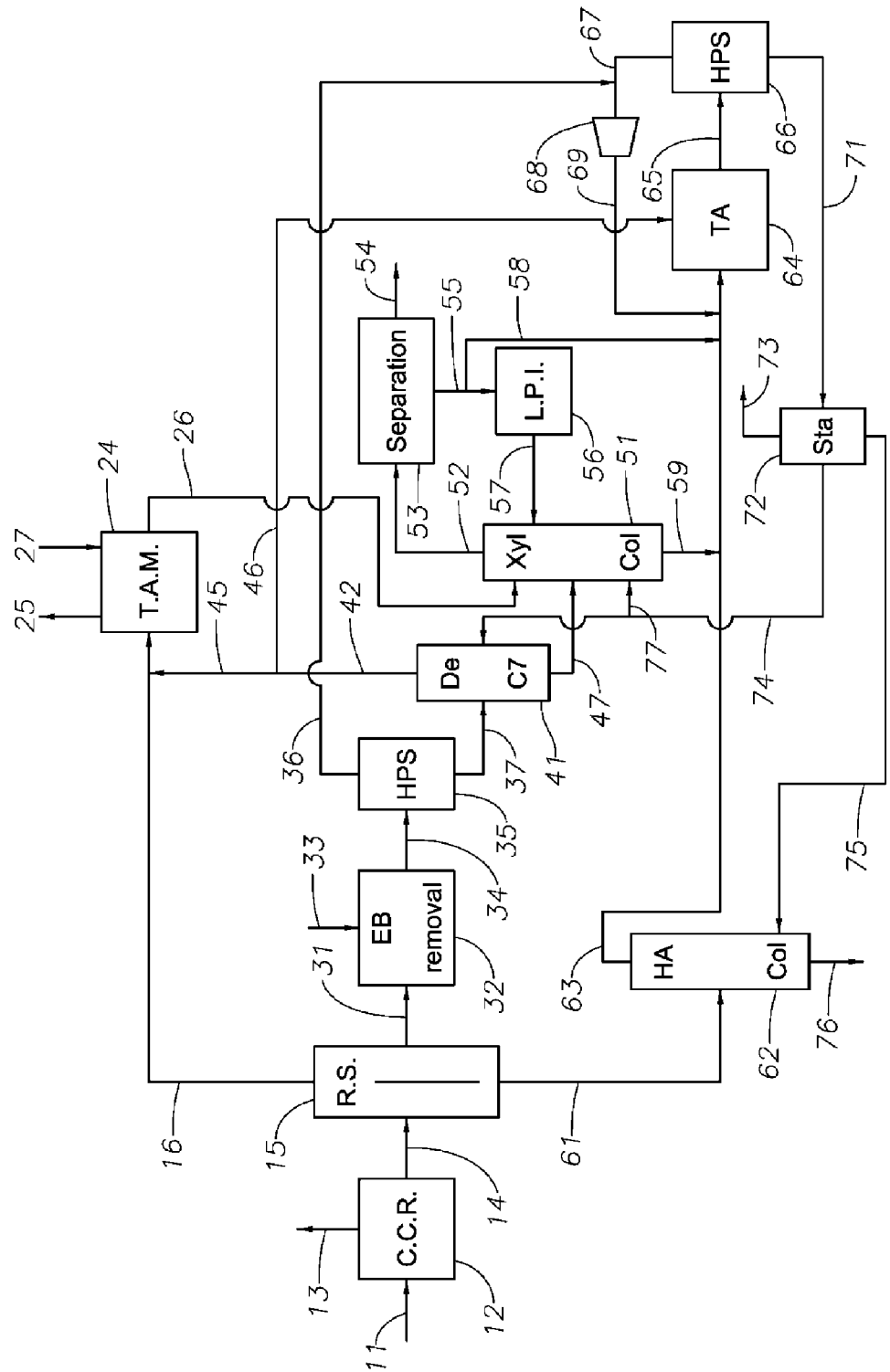
FIG. 2 is a flow diagram of a process for producing para-xylene from catalytic reformate according to a second embodiment of the invention.

One modification of the process shown in FIG. 1 is illustrated in FIG. 2, in which like reference numerals are used to indicate like components to those shown in FIG. 1. In particular, in the process shown in FIG. 2, there is no provision for non-aromatics or benzene recovery and so the extraction section 17 and the benzene column 21 of FIG. 1 are omitted. Thus, in this modification, after the $C_{5-}$ fraction of the reformer effluent is removed in a depentanizer (not shown), the effluent is fed via line 14 to a reformate splitter section 15 which separates a $C_{7-}$-containing overhead stream, a $C_8$-containing intermediate stream, and a $C_{9+}$-containing bottoms stream. The $C_{7-}$-containing overhead stream is fed via line 16 to the toluene methylation section 24, with no benzene extraction step, and, as in the FIG. 1 embodiment, the $C_8$ stream from reformate splitter 15, which also contains some $C_9$ impurities, is collected in line 31 and sent to ethylbenzene removal unit 32, and the $C_{9+}$ bottoms stream from the reformate splitter 15 is sent via line 61 to the heavy aromatics column 62. Another noticeable change affects the overhead of the deheptanizer column 41, collected in line 42. Since benzene recovery is omitted, the stream can be directed to toluene methylation unit 24 via line 45 or to transalkylation unit 64 via line 46 for additional production of xylenes.

A modification of the process shown in FIG. 1 or FIG. 2 is the combination of the two high pressure separators 35, 66 into a single unit (not shown). The modification may require the EB removal unit 32 to operate at the same pressure as the transalkylation unit 64. In that case, the EB removal unit 32 will operate at higher temperature which may increase xylene losses, predominantly in the form of toluene and trimethylbenzene (TMB). The toluene will be converted to xylenes in toluene methylation section 24, while the TMB will be converted to xylenes in transalkylation section 64. Alternatively, both the toluene and TMB can be converted back to xylenes in the transalkylation section 64. Therefore, the net xylenes make across the circuit will remain unaffected by operation of the EB removal unit 32 at a higher temperature, and the equipment can be reduced by combining the high pressure separators.

The invention will now be more particularly described with reference to the following non-limiting Example.

Example 1

This simulated example illustrates how the addition of a toluene alkylation with methanol unit increases the para-xylene output of an aromatics complex based on the same feedstock as a conventional aromatics complex where xylenes are generated in the reforming and transalkylation sections. In this example, it is assumed that all xylenes will be converted to para-xylene (no ortho-xylene production). Alternatively, one fractionation tower may be a divided wall column to produce a para-rich xylene stream and equilibrium xylene stream, thereby saving capital and enjoying the option to optimize feeds to the SMB separation section using line flush technology. The results are shown in Table 1 below.

TABLE 1

| BPD | kta | | | | | | |
|---|---|---|---|---|---|---|---|
| 29000 | 1245.3 | | | | | | |
| | | Xylenes_Recovery (only) | | Xylenes_Recovery and Transalkylation | | Xylenes_Recovery with TAM and Transalkylation | |
| | CCR Reformate | Percent | KTA | Percent | KTA | Percent | KTA |
| H2 | 4.0 | 49.8 | 3.7 | 46.4 | 3.0 | 37.6 | 3.3 | 41.3 |
| C1 | 1.3 | 16.2 | 0 | 0.0 | 0.0 | 0.0 | 0.0 | 0.0 |
| C2 | 2.1 | 26.2 | 0 | 0.0 | 0.0 | 0.0 | 0.0 | 0.0 |
| Fuel | | 0.0 | 5.0 | 62.5 | 10.0 | 127.9 | 10.5 | 130.8 |
| C3 | 2.8 | 34.9 | 0 | 0.0 | 0.0 | 0.0 | 0.0 | 0.0 |
| C4 | 3.5 | 43.6 | 0 | 0.0 | 0.0 | 0.0 | 0.0 | 0.0 |
| LPG | | 0.0 | 6.3 | 78.5 | 6.3 | 78.5 | 6.3 | 78.5 |
| C5 | 2.9 | 36.1 | 0 | 0.0 | 0.0 | 0.0 | 0.0 | 0.0 |
| C6 | 4.4 | 54.8 | 0 | 0.0 | 0.0 | 0.0 | 0.0 | 0.0 |
| C7 | 3.5 | 43.6 | 0 | 0.0 | 0.0 | 0.0 | 0.0 | 0.0 |
| C8 | 0.9 | 11.2 | 0 | 0.0 | 0.0 | 0.0 | 0.0 | 0.0 |
| Raffinate | | 0.0 | 11.7 | 145.7 | 11.7 | 145.7 | 11.7 | 145.7 |
| Bz | 3.5 | 43.6 | 6.7 | 83.6 | 15.7 | 195.7 | 10.9 | 135.2 |
| Tol | 18.0 | 224.2 | 0 | 0.0 | 0.0 | 0.0 | 0.0 | 0.0 |
| Xyl | 24.0 | 298.9 | 0 | 0.0 | 0.0 | 0.0 | 0.0 | 0.0 |
| EB | 4.8 | 59.8 | 0 | 0.0 | 0.0 | 0.0 | 0.0 | 0.0 |
| Px | | 0.0 | 23.0 | 286.9 | 45.0 | 560.9 | 53.1 | 661.8 |
| A9 | 18.0 | 224.2 | 0 | 0.0 | 0.0 | 0.0 | 0.0 | 0.0 |
| A9/10+ | 4.9 | 61.0 | 0 | 0.0 | 0.0 | 0.0 | 0.0 | 0.0 |
| A11+ (FO) | 1.4 | 17.4 | 1.4 | 17.4 | 1.4 | 17.4 | 2.2 | 27.4 |
| Mogas | | 0.0 | 42.1 | 524.3 | 6.8 | 84.9 | 6.1 | 76.0 |
| MeOH (HC) | 0 | 0.0 | 0.0 | 0.0 | 0.0 | 0.0 | -4.1 | -50.6 |

In Table 1, each aromatics complex employs the same feedstock (1245.3 kTa naphthas) qualitatively and quantitatively. Furthermore the reforming section provides the same product slate in all cases, the product slate being listed in column #1 entitled "CCR Reformate". Column #2 entitled "Xylenes Recovery (only)" shows para-xylene production if only reformer xylenes are recovered (no transalkylation unit). Column #3 entitled "Xylenes Recovery and Transalkylation" shows para-xylene production in a conventional aromatics complex, where a transalkylation unit has been added to produce additional xylenes. Column #4 entitled "Xylenes Recovery with TAM and Transalkylation" shows para-xylene production from an aromatics complex where a toluene alkylation with methanol unit has been added to a conventional aromatics complex with a transalkylation unit. This configuration includes an ethylbenzene removal unit as shown in FIG. 1.

As can be seen from Table 1, on the same feedstock and reforming section output basis, para-xylene production for a conventional aromatics complex is 560.9 kTa, while para-xylene production for a conventional complex where toluene alkylation with methanol unit has been added is 661.8 kTa.

Furthermore, para-xylene production is often favored over benzene production due to higher margins. Benzene can be fed to the transalkylation section for additional xylenes production, but this production is limited by methyl to ring ratio. However when a toluene methylation section is available, all benzene can be converted to xylenes—and further to para-xylene—if desired. Hence in the case of column #4, an additional 135.2 kTa of benzene is available for further para-xylene production. In this case, the amount of the complex paraxylene can be increased to 845.5 kta, an increase of nearly 50% para-xylene production over the complex without toluene methylation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing para-xylene, the process comprising:
   (a1) separating a feed stream comprising $C_{6+}$ aromatic hydrocarbons into at least a $C_{7-}$ aromatic hydrocarbon-containing stream, a $C_8$ aromatic hydrocarbon-containing stream, and a $C_{9+}$ aromatic hydrocarbon-containing stream;
   (b1) contacting at least part of the $C_{7-}$ aromatic hydrocarbon-containing stream with a methylating agent under conditions effective to convert toluene to xylenes and produce a methylated effluent stream;
   (c1) contacting at least part of the $C_8$ aromatic hydrocarbon-containing stream with a catalyst effective to dealkylate ethylbenzene and produce an ethylbenzene-depleted $C_8$ aromatic hydrocarbon-containing stream;
   (d1) recovering para-xylene from the methylated effluent stream and the ethylbenzene-depleted $C_8$ aromatic hydrocarbon-containing stream to produce at least one para-xylene depleted stream;
   (e1) contacting at least part of the at least one para-xylene depleted stream with a xylene isomerization catalyst under liquid phase conditions effective to isomerize xylenes in the para-xylene depleted stream and produce an isomerized stream;
   (f1) recycling at least part of the isomerized stream to (d1);
   (g1) contacting at least part of the $C_{9+}$-containing stream with a transalkylation catalyst under conditions effective to convert $C_{9+}$-aromatics to $C_{8-}$-aromatics and produce a transalkylated stream; and
   (h1) recycling at least part of the transalkylated stream to (b1) and (d1).

2. The process of claim 1, wherein the feed stream in (a1) comprises a mixture of $C_{6+}$ aromatic and aliphatic hydrocarbons produced by removing $C_{5-}$ hydrocarbons from a reformate stream.

3. The process of claim 1, wherein the $C_{7-}$ aromatic hydrocarbon-containing stream is subjected to extraction to remove non-aromatics and produce a toluene-containing aromatic stream, wherein the toluene-containing aromatic stream is separated into a benzene stream and a toluene stream, and further wherein the toluene stream is supplied to the contacting (b1).

4. The process of claim 3, wherein a portion of the benzene stream or benzene-containing stream is supplied to the contacting (g1) to optimize the methyl to ring ratio.

5. The process of claim 1, wherein the separating (a1) is conducted by a dividing wall distillation column.

6. The process of claim 3, wherein at least part of the benzene-containing stream is supplied to the contacting (b1).

7. The process of claim 1, wherein the methylating agent comprises methanol.

8. The process of claim 1, wherein contacting (b1) is conducted in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa).

9. The process of claim 8, wherein said porous crystalline material comprises ZSM-5 which has undergone prior treatment with steam at a temperature of at least 950° C.

10. The process of claim 1, wherein part of the $C_{7-}$-aromatics in the transalkylated stream are recycled to the contacting (g1).

11. The process of claim 1 and further comprising:
   (k1) recovering ortho-xylene from at least one of the $C_8$ aromatic hydrocarbon-containing stream, the methylated effluent stream, and the transalkylated stream.

12. The process of claim 1 and further comprising:
   (l1) recovering unconverted toluene from the methylated effluent stream; and
   (m1) supplying the unconverted toluene to the contacting (b1).

* * * * *